Figure 1:
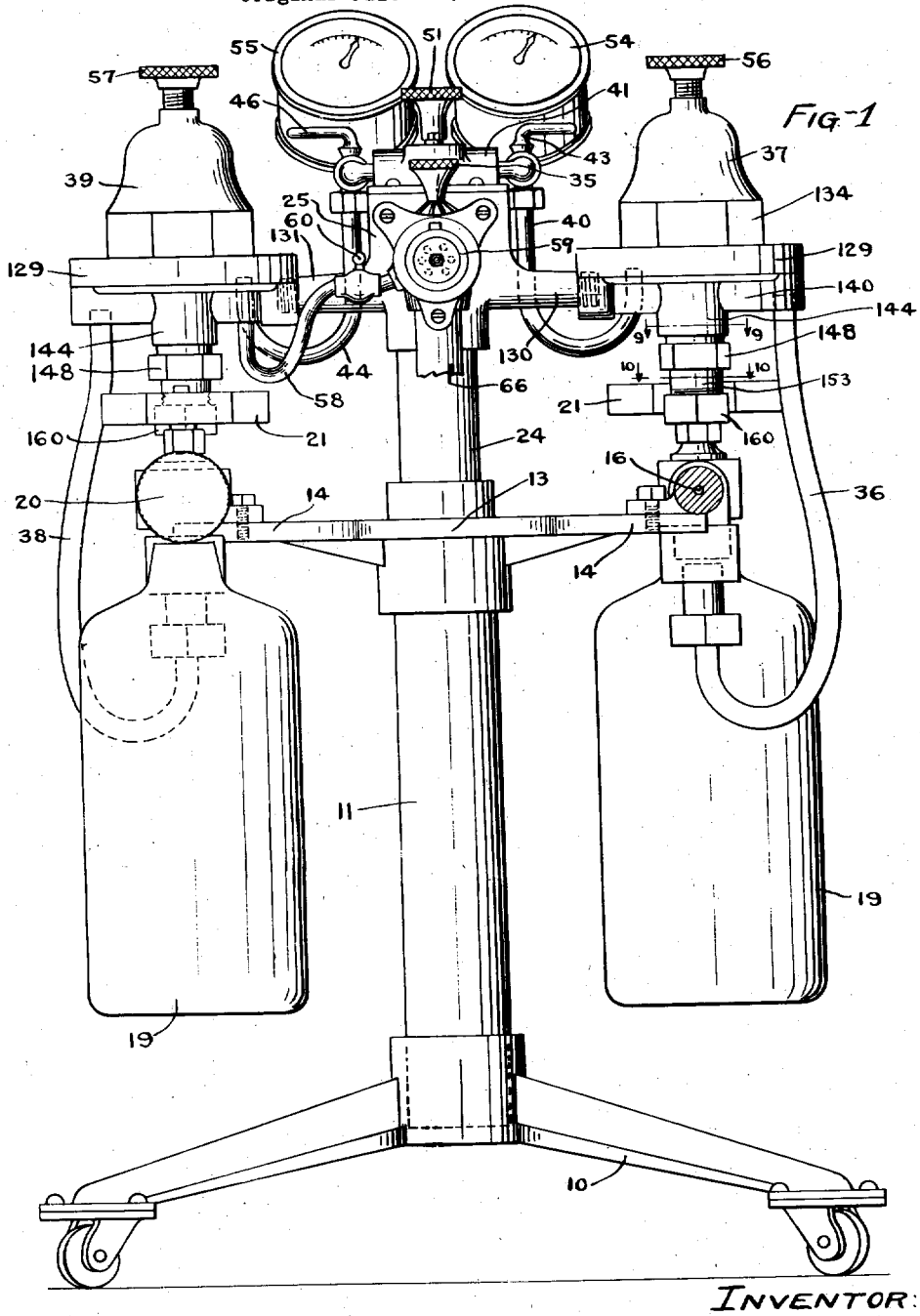

July 22, 1924. Re. 15,874

J. A. HEIDBRINK

APPARATUS FOR DELIVERING A MIXTURE OF GASES

Original Filed Sept. 26, 1912 4 Sheets-Sheet 1

INVENTOR:
JAY A. HEIDBRINK.
BY Whiteley and Ruckman
ATTORNEYS.

July 22, 1924. Re. 15,874

J. A. HEIDBRINK

APPARATUS FOR DELIVERING A MIXTURE OF GASES

Original Filed Sept. 26, 1912 4 Sheets-Sheet 2

INVENTOR:
JAY A. HEIDBRINK.
BY Whiteley and Ruckman
ATTORNEYS.

July 22, 1924. Re. 15,874
J. A. HEIDBRINK
APPARATUS FOR DELIVERING A MIXTURE OF GASES
Original Filed Sept. 26, 1912 4 Sheets-Sheet 3
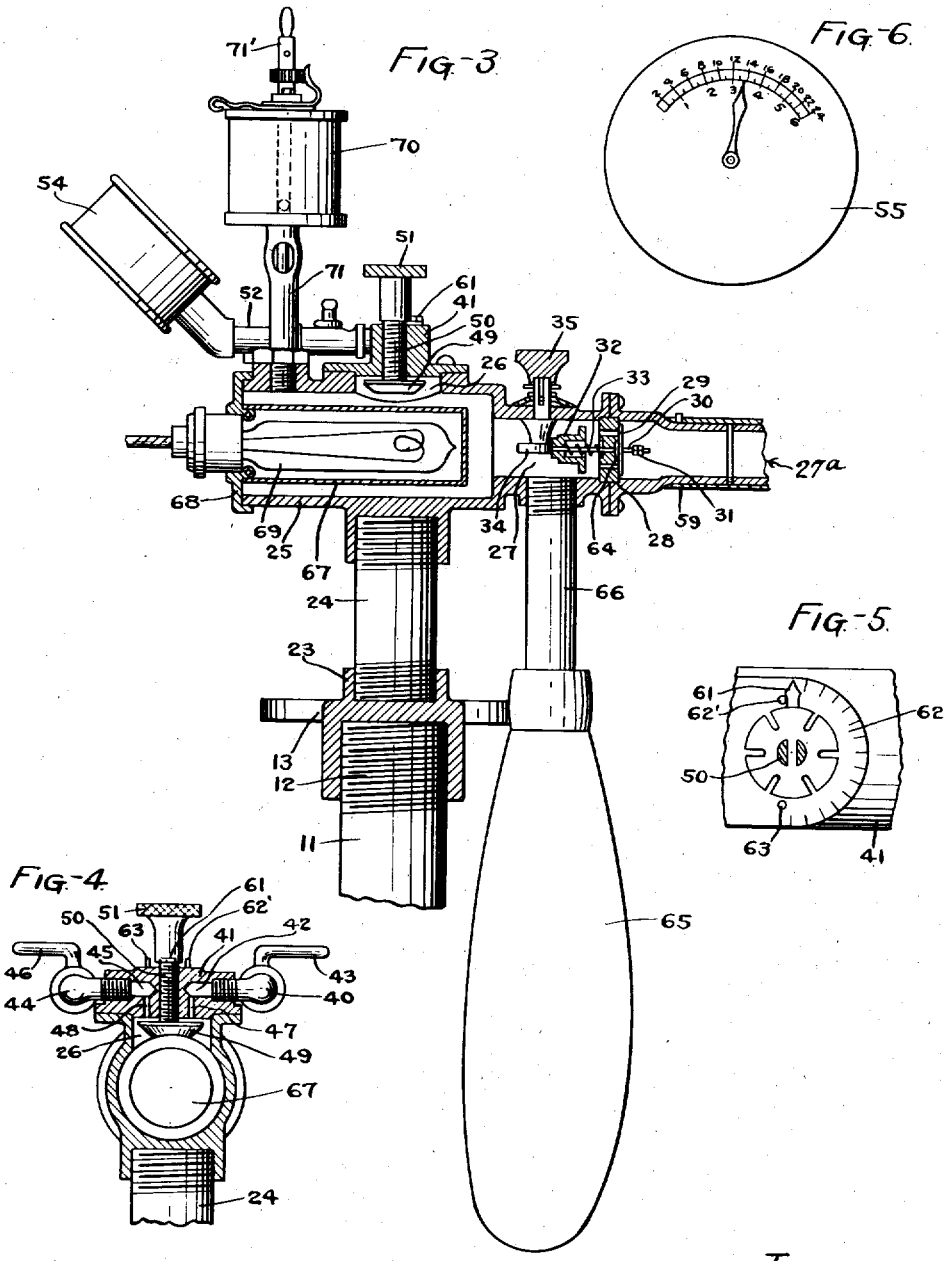
INVENTOR:
JAY A. HEIDBRINK
BY Whiteley and Ruckman
ATTORNEYS.

July 22, 1924. Re. 15,874

J. A. HEIDBRINK

APPARATUS FOR DELIVERING A MIXTURE OF GASES

Original Filed Sept. 26, 1912 4 Sheets-Sheet 4

INVENTOR:
JAY A. HEIDBRINK
BY Whiteley and Ruckman
ATTORNEYS

Reissued July 22, 1924. Re. 15,874

UNITED STATES PATENT OFFICE.

JAY A. HEIDBRINK, OF MINNEAPOLIS, MINNESOTA.

APPARATUS FOR DELIVERING A MIXTURE OF GASES.

Original No. 1,265,910, dated May 14, 1918, Serial No. 722,455, filed September 26, 1912. Application for reissue filed May 2, 1924. Serial No. 710,662.

*To all whom it may concern:*

Be it known that I, JAY A. HEIDBRINK, a citizen of the United States, residing at Minneapolis, in the county of Hennepin and State of Minnesota, have invented certain new and useful Improvements in Apparatus for Delivering a Mixture of Gases, of which the following is a specification.

My invention relates to an apparatus for delivering a mixture of two or more gases to be used as an anesthetic. The invention has for its object primarily to deliver to a gas administering passage and respirator a mixture of two gases, such, for example, as nitrous oxid and oxygen in proper proportions for producing anesthesia in a given patient. And the apparatus embodying my invention provides means for ready and instant control of the flow of gas so that the proportions of gases may be varied at will, but such that when a given proportion of gas is desired more or less of gas mixture in such proportion may be delivered at will to the gas bag and the flow of gas in that proportion be continued indefinitely whatever the rate of flow of the mixture.

It is also an object of my invention to provide means whereby the mixture of gases may be cut off and a single gas such as pure oxygen be fed to the respirator. I also provide means for warming the gas as it passes from the container to the gas bag as well as means for permitting re-breathing where such may be desirable.

The full objects and advantages of my invention will appear in connection with the detailed description thereof and the novel features thereof are particularly pointed out in the claims.

In the drawings, illustrating the application of my invention in one form,—

Figure 2:
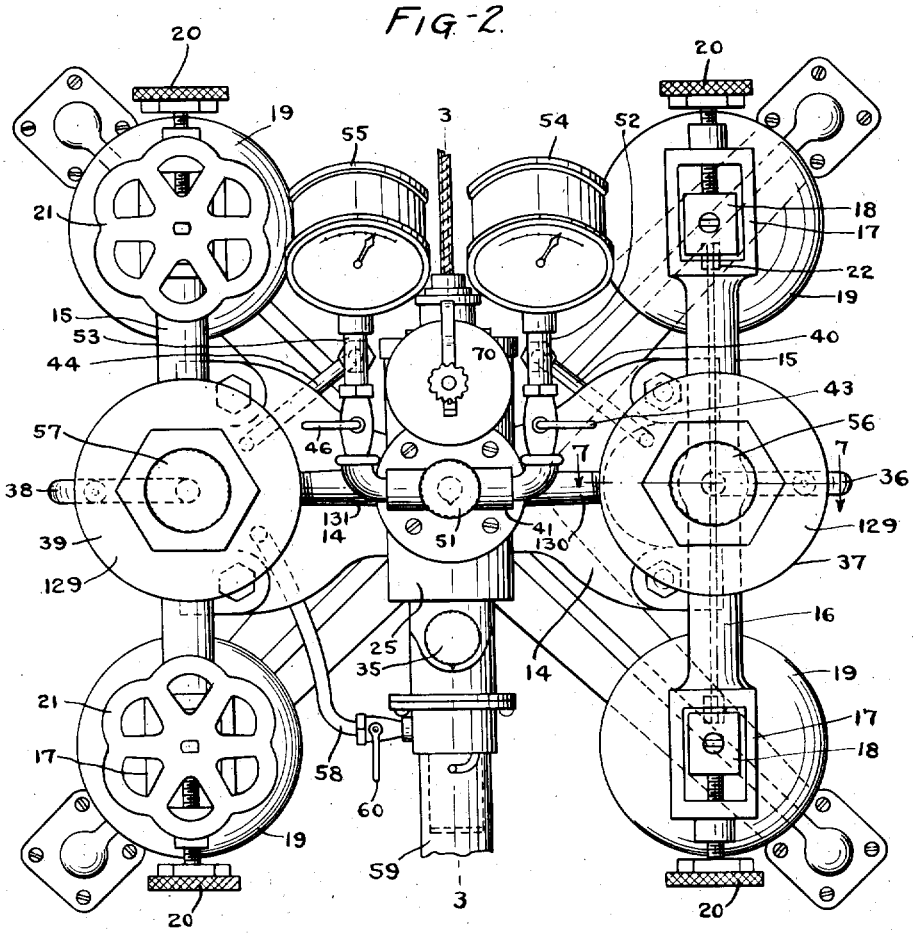
Figure 7:
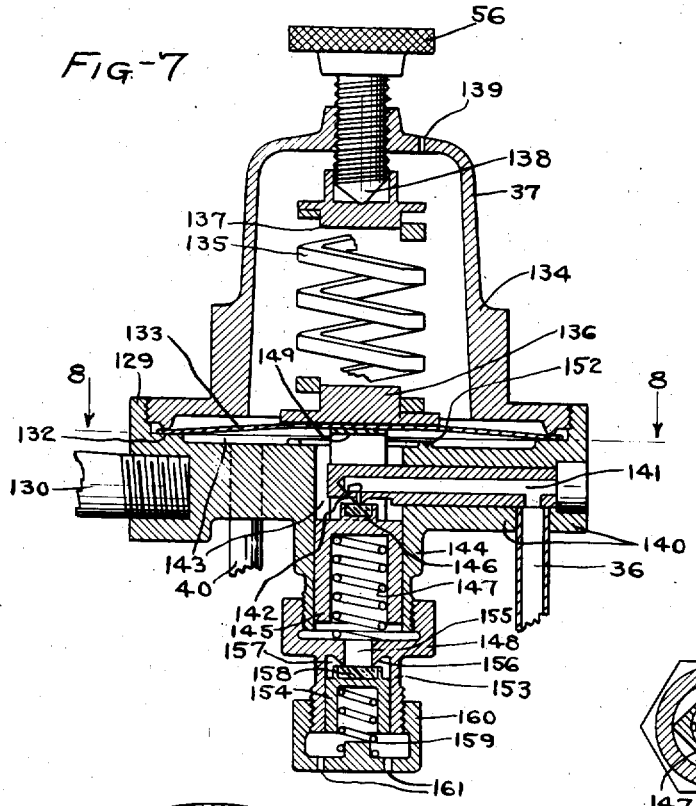
Figure 9:
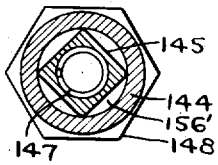
Figure 8:
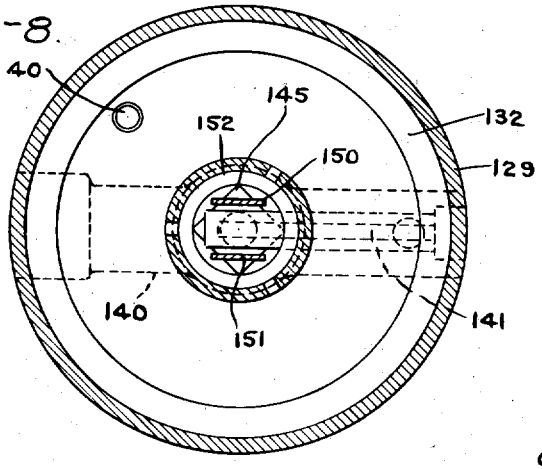
Figure 10:
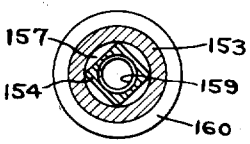

Figure 1 is a side elevation of a gas administering apparatus embodying my invention. Fig. 2 is a plan view of the same. Fig. 3 is a fragmentary sectional elevation on line 3—3 of Fig. 2. Fig. 4 is a sectional view of the valve mechanism shown in Fig. 3 viewed at right angles thereto. Fig. 5 is an enlarged view of the scale for indicating the valve opening. Fig. 6 indicates a form of marking for the dials of the gages. Fig. 7 is a detail sectional view of one of the reducing valves taken on line 7—7 of Fig. 2. Fig. 8 is a sectional plan view taken on line 8—8 of Fig. 7. Figs. 9 and 10 are sectional plan views taken on lines 9—9 and 10—10, respectively, of Fig. 1.

An ordinary base 10 has secured centrally thereon a standard 11 threaded into a socket 12 in a table 13 having a pair of arms 14. Each of the arms 14 has secured thereto a crossbar 15 provided with a valved aperture 16, and each crossbar has at the end thereof a yoke 17 within which the heads 18 of gas containers 19 are adapted to be positioned and secured in communication with the channel of aperture 16 by means of screws 20, the flow of gas from the containers 19 being regulated by hand screws 21. The yokes 17 have a nipple 22 positioned to enter a socket in the heads 18 and the screws 20 force the said nipple within said socket in a gas-tight manner. The containers 19 on one side of the machine will contain nitrous oxid, those on the other side will contain oxygen, where the mixture of gases is to be nitrous oxid and oxygen. As shown in the drawings, containers at the right are charged with nitrous oxid and those at the left with oxygen. Within a socket 23 formed on the top of table 13 is secured by threading or otherwise a short standard 24. Supported upon the standard 24 is a casting 25 having a mixing chamber 26 from which extends a passageway 27. The passageway 27 is provided with a perforated partition 28, a flap valve or vibrating disk 29 operating to close the apertures in partition 28 when the pressure from outside of mixing chamber 26 exceeds the pressure inside said chamber, and correspondingly moving to open said apertures when the higher pressure is within chamber 26. The disk 29 is slidably mounted on a spindle 30 which extends through the partition 28, said spindle being provided with an inside shoulder 64 adapted to seat within an aperture for receiving the same in the partition 28. The spindle 30 also has an outer shoulder 31 spaced from the inner shoulder 64 so that the disk 29 is permitted to vibrate on spindle 30 between the shoulders 64 and 31, a distance sufficient to permit ready passage of the mixture during inhalation. The spindle 30 has on the inner end, inside partition 28, a cap 32 formed to cover the apertures in partition 28 when said cap is brought into engagement therewith. A spring 33 surrounds the spindle 30 and engages a seat in the partition 28 and another seat in the cap 32, operating to push said cap and the spindle inwardly so as normally to bring the shoulder 64 into its recess in the partition 28, in which position disk 29, at its inward movement, will contact with partition 28 and close the apertures therein from the outside, thereby preventing rebreathing. In the position of the parts, as shown in Fig. 3, the cap 32 will just engage the periphery of a cam member 34 protruding within the passageway 27 and operated by a thumb nut 35. Turning the thumb nut will rotate the cam member, moving the cap and spindle, with the shoulders thereon, outward so that shoulder 64 is brought out of its seat and diaphragm 29 can no longer, on its inward movement, engage partition 28 and close the apertures therein. This will permit rebreathing of the anesthetizing mixture; thus the exhalations of the patient may pass through the apertures in partition 28 and into the container or gas bag 65 which opens through connection 66 into passageway 27 inside of partition 28. The extent of rebreathing may be varied by varying the position of spindle 30 and shoulder 64 so that the diaphragm may approach more or less close to partition 28, thereby producing a greater or less opening for rebreathing. If it is desired to close entirely the connection from the respirator with the mixing chamber, cam 34 may be operated to force the cap 32 into engagement with partition 28, thereby closing the apertures therein. Or, if desired, these members may be omitted entirely and the passageway 27 be made continuous with the gas administering passageway 27[a] in the tube 59, which leads to the respirator.

Each of the gas containers comprises a source of supply of gas under pressure and from each of the repective gas containers 19, that for oxygen and also that for nitrous oxid, there is a passageway connection extending to the mixing chamber 26 whereby the respective gases are conducted to the mixing chamber where they become mixed and from whence they are delivered to the gas administering passages. These passageways are similar for each gas. The nitrous oxid gas is admitted by hand wheel 21 into passageway 16 from which it passes to and through a connecting passageway 36 into and through a reducing valve mechanism 37 of well-known construction. The oxygen gas similarly is admitted to its passageway 16 from which it enters a connecting passageway 38 and passes into and through a reducing valve structure 39 in all respects similar to the reducing valve 37. From the reducing valve 37 the nitrous oxid is conducted by a passageway 40 to a valve head 41 secured to the top of the walls of chamber 26, the connection 40 entering a short chamber 42, from whence the nitrous oxid gas passes through a valve structure into the mixing chamber, as clearly shown in Fig. 4, the connection 40 being provided with a cut-off valve 43, as indicated in Fig. 1. Similarly, the oxygen is conducted from the reducing valve 39 through a connection 44 to an independent chamber 45 in the valve head 41, from whence it is delivered past the valve mechanism into the mixing chamber, a cut-off valve 46 being also provided to shut off oxygen from the chamber 45. There is thus a continuous passageway between the nitrous oxid container and the mixing chamber and a separate similar passageway between the oxygen container and the mixing chamber each having a valve at its termination for admitting gas into the mixing chamber and a second valve in each passageway for reducing the pressure of the gas to a relatively low pressure for delivery to the mixing chamber.

The head 41 has the bottom wall thereof forming the roof of the chamber 26, which bottom wall or roof is milled smooth and true. From the chamber 42 an aperture 47 extends into chamber 26 and from chamber 45 an aperture 48 extends into chamber 26. Different proportions of nitrous oxid and oxygen may be employed for an anesthetizing mixture, according to the experience and practice of the operator and the character of anesthesia desirable to produce. In general it may be said that the proportions of oxygen and nitrous oxid to produce analgesia, or the low form of anesthesia, in which the sensory nerves are inactive although reason is retained by the patient, would be something like four parts of nitrous oxid to one part of oxygen. I prefer, therefore, to form the apertures 47 and 48 of such size in relation to the form of valve closure employed that, when the pressures at which the two gases are delivered are equal, four times as much nitrous oxid will pass to the mixing chamber as oxygen. Many different forms of valve closures may be employed to effect this result. The preferred form shown herein, which is subject to easy control, comprises a disk 49 on a shank 50 threaded into the valve head 41, the disk 49 being in the chamber 26 and coming below the apertures 47 and 48, the surface of the disk adjacent to said apertures and the bottom wall of head 41 being milled smooth and true so that when said disk is drawn up against the bottom wall, it will fit tightly therewith and wholly cut off all flow of gas through the apertures 47 and 48. The threaded shank 50 has in the outer end thereof a thumb nut 51 by which the same may be turned, turning of the shank 50 having the effect of moving the disk 49 away from or toward the bottom of the head 41.

The cut-off valves 43 and 46 are formed in short pipe sections 52 and 53 into which the connecting pipes 40 and 44 respectively, deliver, and the pipe section 52 has at the end thereof a gage 54, at all times subject to the pressure of gas delivered from the reducing valve 37. Similarly the pipe section 53 connects with a gage 55 subject at all times to the pressure of gas delivered from reducing valve 39. The reducing valves are subject to complete manual control by means of a hand nut 56 on valve 37 and a hand nut 57 on valve 39. The pressure of the gas being delivered from each of the reducing valves (that is, nitrous oxid from valve 37 and oxygen from valve 39) may thus be instantly and accurately regulated.

These reducing valves, as stated, are of well-known construction, being separately fabricated and sold, and are introduced into the mechanism in the following manner. A base member 129 in each case is secured to arms 130, 131 formed integral with the mixing chamber casting 25. This base member has a cup-shaped portion indicated at 132 upon which rests a diaphragm 133. A cap 134 having a hexagonal portion is screwed into the cup-shaped member 132 and engages and holds the diaphragm in position around its circumferential edges. A compression spring 135 engages a block 136 on the outside of the diaphragm and another block 137 at its upper end, which last-named block in turn is engaged by the nose 138 of the hand nut 56 (57 of valve 29) threaded into the cap 134 whereby a desired degree of pressure is exerted by the spring upon the diaphragm 133, which diaphragm is sealed from atmosphere on its underside but is open to atmosphere on its upper side through the duct 139 in cap 134. An extension 140 of the base casting 129 is provided with a passageway 141 communicating through the pipe 36 with the nitrous oxid containers 19 (or through pipe 38 with the oxygen containers 19). The gas from the passageway 141 may escape through a valve duct 142 into a chamber 143 immediately below the diaphragm 133, from whence nitrous oxid gas continues through passageway 40 (the oxygen going through passageway 44) to the mixing chamber 26. A boss 144 forms a cylindrical continuation of a part of the chamber 143, and within the cylindrical interior of this boss is a rectangular slide 145 carrying at its closed upper end a rubber plug 146 held in a seat integral with the slide 145. A compression spring 147 within the hollow portion of the slide 145 engages its top closure at one end, and a cap nut 148 at the other end whereby the slide, and particularly the rubber plug 146 carried thereby, is forced against the valve duct 142. A yoke member 149 has its two legs 150, 151 engaging the top of the slide 145, while the yoke portion engages the diaphragm 133. A raised annular ring 152 will limit downward movement of the diaphragm 133. Operation of the thumb nut 56 will compress spring 135, which in turn will put pressure upon diaphragm 133 from which the pressure is communicated through the yoke member 149 and its legs 150, 151 to the slide 145, which is thereby caused to move against the pressure of spring 147 to open the valve 142. The admission of gas in the chamber 143 will put the gas pressure upon the underside of the diaphragm 133, tending to push it back against the pressure of spring 135, thus releasing the pressure of said spring from the yoke member 149 and permit spring 147 to reseat the rubber plug 146, cutting off flow of gas. In this manner the delivery pressure of gas through the passageway 40 is regulated to be greater or less according to the amount of pressure or compression exerted through spring 135.

The cap 148 is hexagonal in its outer contour, as shown in Fig. 1, whereby the pressure upon spring 147 may be varied. This cap has cast therewith a boss 153 having a cylindrical interior chamber in which is a rectangular slide 154 corresponding with slide 145. A duct 155 communicates from the chamber 156′ formed around the slide 145 with a corresponding chamber 157 formed around the slide 154 with a valve seat 156 protruding downwardly around said duct. The slide 154 carries a rubber plug 158 which is forced into engagement with the valve portion 156 by a spring 159 seated in the slide 154 and engaging a hexagon-shaped cap 160 provided with apertures 161 at its outer end. The cap 160 is threaded upon the boss 153 by means of which the desired amount of compression of spring 159 is obtained. The duct 155 is very much larger than the duct 142 and is subject to the pressure of gas at any time in chamber 143 and the communicating chamber 156 so that if the pressure of gas for any reason in chamber 143 should rise beyond a desired extent the plug 158 will be forced outwardly and the gas will escape through chamber 157 and ducts 161.

The gas passageways, then, from the containers to the mixing chamber comprise the duct 16, passageway 36, chamber 143 within the reducing valve 37, passageway 40, chamber 42 and aperture 47 for the nitrous oxid, while the corresponding but wholly independent passageway for the oxygen comprises a duct 16, a passageway 38, the chamber 143 in the reducing valve 39, the passageway 44, the chamber 45 and the aperture 48 extending therefrom to the valve plate in the mixing chamber.

The apertures 47 and 48, as here shown, have a relative delivery capacity of four to one, and means is here provided on the respective gages, specifically as shown on the oxygen gage, by which the proportions of the oxygen gas in any of the mixtures going to the patient may be immediately determined by inspection. It will be noted that the gages 54 and 55, for nitrous oxid and oxygen respectively, will be in all respects identical, and each may suitably be such as will register a maximum pressure of six pounds, which is such a gage as would be practicably desirable in an apparatus of this character. The scales on each of the gages will, of course, comprise the usual figures, running from one pound to six pounds, and at least subdivided into fourths for indicating pressures from zero to one-fourth pound and upward to six pounds. The nitrous oxid scale in practice will show only the pressures at which this gas is being delivered. Upon the oxygen gage I form a second scale comprising figures up to twenty four or higher for indicating the percentage of oxygen in the mixture of gases being delivered at the indicated oxygen pressure when the pressure of the nitrous oxid as indicated upon its scale is at a predetermined point; that is the needle of the oxygen gage will indicate the delivery pressure of oxygen on the pressure scale and at the same time will indicate on the second scale the percentage of oxygen being delivered in the mixture of gases passing to the gas bag and respirator. This percentage scale is, for any one gage, developed only for one fixed or predetermined pressure of the nitrous oxid as indicated by the nitrous oxid pressure gage scale. In the scale construction shown in Fig. 6 of the drawings, the oxygen percentage scale is developed to show the percentages of oxygen in the mixture of gases going to the patient when the nitrous oxid pressure, as shown by the nitrous oxid gage, is at five pounds, this being a satisfactory and convenient pressure for nitrous oxid. It will be understood that the pressure indication of either gage is controllable at will by means of the thumb screws 56 and 57 of the reducing valves, so that it will always be practicable to have a fixed reading upon the nitrous oxid gage, this being, as shown, five pounds. In varying the proportion of oxygen in the mixture, it will usually only be necessary to vary the pressure at which the oxygen is delivered to the mixing chamber, and such variation will not only show on the gage the pressure at which oxygen is being delivered, but on the second scale will show the actual percentage of oxygen going into the mixture which the patient is breathing. This is true, in the gage shown in Fig. 6, only when the gage for nitrous oxid is set to deliver nitrous oxid at a pressure of five pounds, to which the secondary scale for percentages of oxygen is graduated. It will thus be seen that the proportion of gases going to the patient is controllable at will and instantly by the operator through the thumb screws 56 and 57, although practically where a mixture is delivered, owing to the ratio of size of the delivery apertures of the respective gases, there will always be a much greater quantity of nitrous oxid in the mixture than of oxygen. A connection 58 is provided extending from reducing valve 39 to the passageway 59 leading from beyond the diaphragm 28 to the respirator, which connection is controlled by a cut-off valve 60. If it is desired at any time to give the patient pure oxygen to effect quick stimulus, the screw 35 and cam 34 may be turned to close the openings from passage 27 through diaphragm 28 and valve 60 opened, admitting oxygen directly to the patient.

The volume of mixture being delivered through mixing chamber 26 is absolutely controlled by the thumb nut 51 operating the valve disk 49, which, cooperating with the apertures 47 and 48, really comprises a double valve for simultaneously increasing or decreasing the rate of the flow of the nitrous oxid through aperture 47 and the oxygen through aperture 48 into the mixing chamber, each in the same proportional amounts, since the actual delivery opening of each valve will comprise the lateral area of a cylinder determined by the diameter of the respective apertures and the distance that the plate or disk 49 is moved away from the valve head through which the apertures extend. Since the areas of the bases of the cylinders are constant, the ratio of the lateral areas, that is the discharge openings, will not be changed by increasing or decreasing the length of the cylinders in the same amount, that is moving the valve plate 49 toward or from the valve aperture wall. In this connection it is to be understood that the actual extent of movement of the valve plate 49 will always be very small and can never be greater than the maximum capacity of the small oxygen aperture 48. The showing in the drawings has of necessity been greatly exaggerated.

As shown in Fig. 5, the shank 50 of the thumb nut 51 is provided with a pointer 61 which covers a scale disk 62 on the top of the portion 41 forming the valve chamber. Pins 62′ and 63 limit movement of the pointer 61 to a little more than half a full turn of screw 51, which amount of turning will open the apertures 47 and 48 for maximum delivery of the gas in whatever proportion is indicated by the relative pressures shown on the two gages 54 and 55. The second pin 63 is necessary since, if the valve were open beyond the maximum capacity of the smaller aperture, the proportion of gases being delivered would no longer remain as indicated, but gas from the larger aperture would be delivered at a relatively greater rate than from the smaller aperture. The pins 62′ and 63 are so positioned relative to the right line movement of valve disk caused by the thread of shank 50 as to produce the above indicated result. It is obvious that if the pitch of the threads on shank 50 were made sufficiently small a single pin 62′ might be employed to be engaged on either side by the pointer 61 and the thumb screw 51 and thereby be capable of practically a complete turn. In this particular it will be noted that a very slight turn of screw 51 will open to an appreciable extent the delivery apertures 47 and 48. When, however, any opening is made the respective gases will flow into the chamber 26 in the proportion indicated, and will always flow in that proportion whether the valve is opened little or much of its maximum capacity. The movements of the valve are controlled with the greatest ease by the operator and will always result in delivering the exact proportion of gas which is desired. The operation of the thumb nut 35 and cam 34 regulating the movement of head 32 and spindle 30 will determine the extent of rebreathing and will regulate this as desired. If the disk 29 has a relatively large amount of freedom of travel upon the spindle 30 and yet can always come back against diaphragm 28, there will be little or no rebreathing. If, however, cam 34 is turned so as to push the shoulder 64 on spindle 30 far enough out so that disk 29 cannot come back into contact with diaphragm 28, rebreathing will be permitted in proportion to the distance away from diaphragm 28 at which disk 29 is being held, it being noted of course that the usual gas bag 65 opens through a connection 66 into passageway 27 extending from mixing chamber 26.

As clearly shown in Fig. 3, the mixing chamber 26 is oblong in shape, and within said chamber and spaced from the inner walls thereof is a closed thin walled casing 67 opening outwardly through an aperture in the end wall 68 of chamber 26. Within the interior of casing 67 is inserted an ordinary incandescent electric light 69 or other electric heating device, as may be desired. The gases entering through apertures 47 and 48 will pass over the edges of valve disk 49 and flow around the heated casing 67 on the way out through passage 27, and are thereby warmed to the desired extent before breathing. In certain cases it is desirable to administer ether or other anesthetic either in combination with one or both of the gases forming the usual mixture, or separately, and to accomplish this I provide an ether cup 70 having a connection through a tube 71 into chamber 26, said ether cup being provided with a dropper mechanism 71′ of usual construction. The ether will drop upon the heated casing 67 and vaporizing will pass into the respirator tube and gas bag either separately or as part of the mixture, according as the same may be used.

I claim:

1. A gas administering machine comprising a plurality of sources of fluid supply, a mixing chamber, means for causing each of said gases to be delivered into the mixing chamber at a definite rate of flow so as to produce a mixture of said gases of predetermined proportions, and means for simultaneously changing the rate of flow of each of said gases into the mixing chamber in the same proportional amount.

2. A gas administering machine comprising a plurality of sources of fluid supply, a mixing chamber, means for causing each of said gases to be delivered into the mixing chamber at a definite rate of flow so as to produce a mixture of said gases of predetermined proportions, an inhaler connected with said mixing chamber for delivering the mixture of gases to the patient as said mixture is produced, and means for simultaneously increasing the rate of flow of each of said gases into the mixing chamber in the same proportional amount for the purpose of forcing an increased amount of said identical mixture of gases to the patient.

3. A gas administering machine comprising a plurality of sources of fluid supply, a mixing chamber, a passageway leading from each of said sources of supply to the mixing chamber for conducting each of said gases separately into the mixing chamber, two valves in each of said passageways, one valve in each passageway being controlled in its operation of delivering gas by the pressure of the gas being delivered from said valve, means under the control of the operator for operating a valve in each passageway for fixing the rate of flow of each of said gases so as to produce a mixture thereof of predetermined proportions, and means under the control of the operator for simultaneously operating the other valve in each passageway so as to simultaneously change the rate of flow of each of said gases into the mixing chamber in the same proportional amount.

4. A gas administering machine comprising a plurality of sources of fluid supply, a mixing chamber, a passageway leading from each of said sources of supply to the mixing chamber for conducting each of said gases separately into the mixing chamber, a valve in each of said passageways operable to cause each of said gases to be delivered into the mixing chamber at a definite rate of flow so as to produce a mixture of said gases of predetermined proportions, an inhaler connected with said mixing chamber for delivering the mixture of gases to the patient as said mixture is produced, a second valve in each of said passageways and means for simultaneously operating said second valve so as to increase the rate of flow of each of said gases into the mixing chamber in the same proportional amount for the purpose of forcing an increased amount of said identical mixture of gases to the inhaler and the patient.

5. A gas administering machine comprising a source of oxygen supply and a source of nitrous oxid supply each under pressure, a mixing chamber, a passageway leading from the oxygen supply and from the nitrous oxid supply to the mixing chamber for conducting each of said gases separately into the mixing chamber, means cooperating with said respective passageways for causing the gases to be delivered to the mixing chamber at reduced pressures, means for determining the rate of flow of each of said gases at such reduced pressures so as to produce a mixture thereof in predetermined proportions, and manually-operative means exterior of but cooperating with said passageways for simultaneously changing the rate of flow of each of said gases into the mixing chamber in the same proportional amount.

6. A gas administering machine comprising a source of oxygen supply and a separate source of nitrous oxid supply, a mixing chamber, a passageway leading from the oxygen supply and another passageway leading from the nitrous oxid supply to the mixing chamber for conducting each of said gases separately into the mixing chamber, two controlling valves in each of said passageways, means under the control of the operator for operating a valve in each passageway for fixing the rate of flow of the oxygen and of the nitrous oxid respectively so as to produce a mixture thereof of predetermined proportions, and means under the control of the operator for simultaneously operating the other valve in each passageway so as to simultaneously change the rate of flow of each of said gases into the mixing chamber in the same proportional amount.

7. A gas administering machine comprising a plurality of sources of fluid supply under pressure, a mixing chamber, a passageway leading from each of said sources of supply to the mixing chamber for conducting each of said gases separately into the mixing chamber, two valves in each of said passageways, means under the control of the operator for operating one valve in each passageway for controlling the respective pressures at which the several gases are delivered to the mixing chamber, other means in said passageways for determining the relative rate of flow of each of said gases into the mixing chamber at fixed relative pressures so as to produce a mixture thereof of predetermined proportions, and means under the control of the operator for simultaneously operating the other valve in each passageway so as to simultaneously change the rate of flow of each of said gases into the mixing chamber in the same proportional amount.

8. A gas administering device having a mixing chamber, means for conducting independently and through separated valve openings a plurality of gases into said chamber in fixed relative proportions, an integral valve member controlling the valve openings for both of said conducting means and having parts held in the same relation to the points of discharge therefrom, and means to move the valve members uniformly in reference to said discharge openings to vary at will the aggregate volume of flow of gases into the mixing chamber while maintaining their respective delivery proportions constant.

9. A gas administering device having a mixing chamber provided with a plane-faced wall and having independent separated valve apertures opening through said wall, means for conducting a plurality of gases from independent sources of supply independently through each of said valve apertures into the chamber in predetermined relative proportions, a valve closure having a plane-surfaced wall held fixed in spaced parallel relation with said wall of the chamber for controlling the flow of gases through said valve apertures, and means to move the valve closure bodily so that the plane face thereof will be caused uniformly to approach or recede from said wall to vary at will the aggregate flow of gases into the mixing chamber while maintaining their respective delivery proportions constant.

10. A gas administering device having a mixing chamber, a valve head having a plane surface on one side forming a part of a wall of said chamber, said valve head being provided with a plurality of independent cavities and having independent valve apertures leading from said cavities into the mixing chamber, means for conducting a different gas into each of said cavities and to the valve apertures, a valve disk within the mixing chamber having a smooth face cooperating with said plane-surfaced wall to control all of said valve apertures, and means under the control of the operator to move the valve disk bodily and uniformly toward and from said valve apertures.

11. A gas administering device having a mixing chamber and a plurality of separated valve apertures extending through a wall of said mixing chamber, means for conducting different gases at fixed relative pressures independently into the mixing chamber through each of said valve apertures, a single unitary valve member within the mixing chamber having portions cooperating with and controlling the delivery openings of the respective valve apertures, and means to move the valve member so that said portions will be caused uniformly to approach and recede from the respective valve apertures.

12. A gas administering device having a mixing chamber and a plurality of separated valve apertures extending through a wall of said mixing chamber, said valve apertures varying in size for delivering fixed relative proportions of the gases when the delivery pressures of the gases are equal, means for conducting different gases at fixed relative pressures independently into the mixing chamber through each of said valve apertures, a single unitary valve member within the mixing chamber having portions cooperating with and controlling the delivery openings of the respective valve apertures, means to move the valve member so that said portions will be caused uniformly to approach and recede from the respective valve apertures, and means limiting movement of said valve member so that the maximum movement thereof away from the valve apertures will open the smallest aperture only to its maximum capacity.

13. A gas administering device comprising separate containers of fluid under pressure, a mixing chamber and means for conducting said fluids independently thereto through separate valve openings, a unitary valve member within the chamber adapted to block both of said openings, and means to move the valve member definitely and uniformly through predetermined distances so that the opening-blocking portions thereof shall be caused to recede from or to approach both said valve openings uniformly.

14. A gas administering device comprising separate containers of fluid under pressure, a mixing chamber provided with a plane-faced wall and having independent valve apertures opening through said wall, means for conducting the gases from said containers independently through each of said valve apertures into the chamber, a thumb-nut having a threaded shank extending through said wall and into said chamber adjacent said valve apertures, a valve plate secured to the end of said shank in said chamber and having a plane face adjacent and parallel with the plane face of the wall and overlying said valve apertures so that rotation of the shank and plate by means of the thumb-nut will move the plate bodily away from or toward the face of said wall and said valve apertures to vary at will the aggregate volume of flow of gases into the mixing chamber without varying their relative delivery pressures.

15. A gas administering device comprising separate containers of fluid under pressure, a mixing chamber, means for conducting the gases independently from said containers and delivering them into said chamber so that the relative proportion of the gases will be unchanged by the delivery means and can be varied only by varying the relative delivery pressures of the gases, means to regulate at will the delivery pressures of each of said gases, means to indicate the pressures at which said gases are delivered for determining the relative proportions of gases going into the chamber and the quality of mixture produced, and means for regulating and controlling the aggregate volume of flow of gases into the mixing chamber while maintaining unchanged the proportions determined by the delivery and pressure-controlling means.

16. A gas administering device comprising a pair of separate containers one having nitrous oxid and the other oxygen stored under pressure therein, a mixing chamber, means for conducting said gases independently from the containers to the mixing chamber, means in said conducting means for varying at will the relative pressures at which said gases are delivered, independent gages each having connection with one of said conducting means and each provided with a scale for indicating the pressure at which gas is being delivered, the oxygen gage being provided with a scale for indicating the percentage of oxygen in the mixture of gases being delivered at the indicated oxygen pressure when the pressure of the nitrous oxid as indicated upon its scale is at a predetermined point.

17. A gas administering device comprising a pair of separate containers one having nitrous oxid and the other oxygen stored under pressure therein, a mixing chamber, means for conducting said gases independently from the containers to the mixing chamber including separated delivery apertures having different relative discharge areas for delivering proportions of the respective gases such as to produce a mixture of the desired quality when the pressures of the gases are equal, means in said conducting means for separately regulating the delivery pressures of the respective gases, means for determining the delivery pressures of said gases so that said pressures may be equalized, and means limited in operation to permit no more than maximum flow of gas through the smallest aperture for varying the aggregate volume of flow of said gases into the mixing chamber while maintaining the proportions determined by the delivery apertures and the delivery pressures of the gases.

18. A gas administering device having a mixing chamber, a respirator tube connected with the mixing chamber, a disk therein, a gas bag having connection with the mixing chamber on the inner side of said disk, and means controlled by the position of the disk so as to permit breathing of gas mixture from the mixing chamber at all times and to prevent or permit, as desired, entrance of the exhalations of the patient to the gas bag and consequent rebreathing of the gas mixture.

19. A gas administering device having a mixing chamber, a respirator tube connected with the mixing chamber having a perforated partition, a gas bag having connection with the mixing chamber on the inner side of said partition, a disk normally cooperating with said partition to open and close communication with the mixing chamber and gas bag during breathing so as to permit breathing of the gas mixture and prevent rebreathing, and controllable means for holding said disk spaced from the partition during exhalation of the patient to permit rebreathing.

20. A gas administering device having a mixing chamber, a respirator tube connected with the mixing chamber having a perforated partition, a gas bag having connection with the mixing chamber on the inner side of said partition, a disk normally cooperating with said partition to open and close communication with the mixing chamber and gas bag during breathing so as to permit breathing of the gas mixture and prevent rebreathing, a spindle on which said disk vibrates between fixed stops, and controllable means for moving said spindle bodily endwise so as to position the stops thereon so that the disk will be held spaced from said partition during exhalation to permit rebreathing of gas mixture.

I testimony whereof I affix my signature hereby.

JAY A HEIDBRINK.